(12) United States Patent
Keefer et al.

(10) Patent No.: US 7,985,260 B2
(45) Date of Patent: Jul. 26, 2011

(54) ACETABULAR PROSTHESIS SYSTEM

(75) Inventors: Ryan C. Keefer, Fort Wayne, IN (US);
Jeffrey A. Rybolt, Fort Wayne, IN (US);
Hengda D. Liu, Warsaw, IN (US);
Matthew D. Smith, Akron, IN (US);
Gerhard J. A. Drescher, Warren, MI (US)

(73) Assignee: DePuy Products, Inc., Warsaw, IN (US)

(*) Notice: Subject to any disclaimer, the term of this patent is extended or adjusted under 35 U.S.C. 154(b) by 351 days.

(21) Appl. No.: 12/164,957

(22) Filed: Jun. 30, 2008

(65) Prior Publication Data

US 2009/0326670 A1    Dec. 31, 2009

(51) Int. Cl.
*A61F 2/32* (2006.01)

(52) U.S. Cl. ............... 623/22.35; 623/22.22; 623/22.36

(58) Field of Classification Search .................. None
See application file for complete search history.

(56) References Cited

U.S. PATENT DOCUMENTS

| | | | |
|---|---|---|---|
| 4,479,271 A * | 10/1984 | Bolesky et al. | 623/20.17 |
| 5,176,711 A | 1/1993 | Grimes | |
| 5,192,329 A * | 3/1993 | Christie et al. | 623/22.22 |
| 5,326,368 A | 7/1994 | Collazo | |
| 5,370,704 A | 12/1994 | DeCarlo, Jr. | |
| 7,291,177 B2 | 11/2007 | Gibbs | |
| 2005/0021148 A1 | 1/2005 | Gibbs | |
| 2006/0241781 A1* | 10/2006 | Brown et al. | 623/23.43 |
| 2007/0088443 A1 | 4/2007 | Hanssen et al. | |
| 2007/0129809 A1 | 6/2007 | Meridew et al. | |
| 2007/0173948 A1 | 7/2007 | Meidew et al. | |
| 2008/0021568 A1 | 1/2008 | Tulkis et al. | |
| 2009/0204225 A1* | 8/2009 | Meridew et al. | 623/22.21 |

OTHER PUBLICATIONS

European Search Report for European Patent Application No. 09163231.5-2310, Aug. 28, 2009, 6 pgs.

* cited by examiner

*Primary Examiner* — David H Willse
*Assistant Examiner* — Javier G Blanco
(74) *Attorney, Agent, or Firm* — Barnes & Thornburg LLP

(57) ABSTRACT

An acetabular prosthesis system configured to be coupled to a surgically-prepared acetabulum includes an acetabular shell, an augment component, and a fastener configured to couple the acetabular shell and the augment component together.

13 Claims, 7 Drawing Sheets

ACETABULAR PROSTHESIS SYSTEM

TECHNICAL FIELD

The present disclosure relates generally to a system and method for use in orthopaedic surgery, and particularly to a modular acetabular prosthesis and augment component for use during the orthopaedic surgical procedure.

BACKGROUND

In hip replacement surgeries, a prosthetic acetabular cup is positioned in the acetabulum and coupled to the patient's hipbone. An acetabular cup typically includes an outer shell configured to engage the patient's hipbone and an inner bearing or liner coupled to the shell and configured to engage a femoral prosthesis. Oftentimes, a portion of the patient's hipbone adjacent the acetabulum is damaged or diseased. These damaged or diseased portions are typically removed by the surgeon and replaced by an augment component. The augment component is typically secured to the patient's hipbone after which the outer shell of the acetabular cup is properly placed and secured to the augment component. Bone cement may be used to secure the augment component to the hipbone and to secure the augment component to the outer shell.

SUMMARY

According to one aspect of the present disclosure, an acetabular prosthesis system configured to be coupled to a surgically-prepared acetabulum of a patient's hipbone includes an acetabular shell and an augment component configured to be coupled to the acetabular shell. The acetabular shell includes an outer curved surface configured to engage the surgically-prepared acetabulum, an inner curved surface, and a plurality of apertures extending through the outer curved surface and the inner curved surface. The augment component is configured to be received within a void created in the surgically-prepared acetabulum and includes an inner curved surface configured to engage the outer curved surface of the acetabular shell, an outer surface, and a slot extending through the inner curved surface of the augment component and the outer surface of the augment component. A first fastener of the prosthesis is configured to extend through at least one of the plurality of apertures of the acetabular shell and into the slot of the augment component in order to couple the acetabular shell and the augment component together.

In one illustrative embodiment, the augment component may include a bore configured to receive a second fastener therethrough. Such a bore may be threaded or non-threaded. In embodiments where the bore is non-threaded, the augment component may be configured for the fastener to be self-threaded into the slot of the augment component.

In another illustrative embodiment, the outer surface of the augment component may be curved. Further, the augment component may include a generally flat end surface. Illustratively, the slot of the augment component may define a plane generally perpendicular to the generally flat end surface of the augment component. Further illustratively, the bore of the augment component may extend through the outer curved surface of the augment component and the generally flat end surface of the augment component.

In still another embodiment, the augment component may be made from a porous metal material. Illustratively, the porous material may be titanium foam.

In yet another embodiment, the radius of curvature of the inner curved surface of the augment component may be generally equivalent to the radius of curvature of the outer curved surface of the shell. Alternatively, the radius of curvature of the inner curved surface of the augment component may be 90%-100% of the radius of curvature of the outer curved surface of the shell.

According to another aspect of the present disclosure, an acetabular prosthesis system configured to be coupled to a surgically-prepared acetabulum of a patient's hipbone includes an acetabular shell, an augment component, and a fastener configured to secure the acetabular shell to the augment component. Illustratively, at least one of the acetabular shell and the augment component includes a slot extending therethrough. The acetabular shell includes an outer curved surface configured to engage the surgically-prepared acetabulum and an inner curved surface. The augment component is configured to be received within a void in the surgically-prepared acetabulum of the patient's hipbone and includes an inner curved surface configured to engage the outer curved surface of the acetabular shell.

In one illustrative embodiment, the acetabular shell may include the slot and the augment component may include a bore configured to receive the fastener therethrough.

In another illustrative embodiment, the augment component may include the slot. Further, a curved body of the acetabular shell may be devoid of any slot or aperture configured to receive the fastener therethrough. Illustratively, the curved body of the acetabular shell may be made from a porous metal such as titanium foam, for example.

In yet another illustrative embodiment, the acetabular shell is able to be secured by the fastener to the augment component in first, second, third, and fourth orientations. Illustratively, in the second orientation the acetabular shell may be moved in one of a medial and a lateral direction relative to the position of the acetabular shell in the first orientation. Further illustratively, in the third orientation the acetabular shell may be moved in one of an anterior and a posterior direction relative to the position of the acetabular shell in the first orientation. In the fourth orientation, the acetabular shell may be moved in one of a superior and an inferior direction relative to the position of the acetabular shell in the first orientation.

According to still another aspect of the present disclosure, a method of implanting an acetabular prosthesis system in a surgically-prepared acetabulum, includes implanting an augment component within a void created in the surgically-prepared acetabulum and coupling the augment component to the surgically-prepared acetabulum. The method further includes positioning an acetabular shell in the acetabulum and orienting the acetabular shell to align a slot of the augment component with at least one aperture of the acetabular shell, and coupling the acetabular shell to the augment component.

In one embodiment, coupling the acetabular shell to the augment component may include driving a fastener through the bore of the acetabular shell and the slot of the augment component. Illustratively, the fastener may include a self-tapping bone screw.

In another illustrative embodiment, the acetabular shell may be coupled to the augment component before the augment component is coupled to the surgically-prepared acetabulum. Alternatively, the acetabular shell may be coupled to the augment component after the augment component is coupled to the surgically-prepared acetabulum.

In yet another illustrative embodiment, coupling the acetabular shell to the augment component may include drilling a fastener through the acetabular shell and into the augment component. The fastener may also be drilled through the acetabular shell, through the augment component, and into the patient's hipbone.

BRIEF DESCRIPTION OF THE DRAWINGS

The detailed description particularly refers to the accompanying figures in which.

DETAILED DESCRIPTION OF THE DRAWINGS

Figure 1:
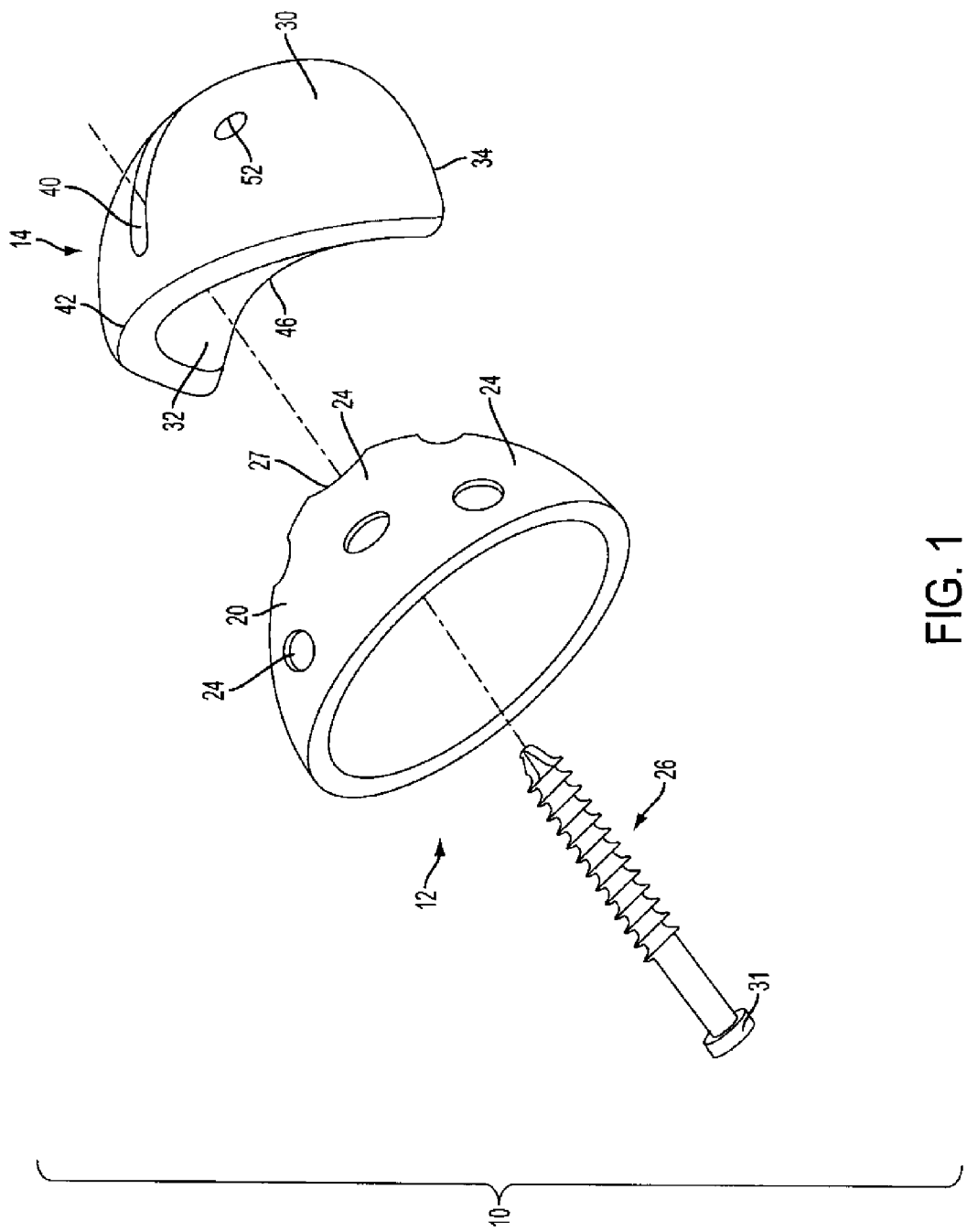
FIG. 1 is an exploded, perspective view of an acetabular prosthesis system including an acetabular shell, an augment component, and a screw for coupling the shell and augment component together.

While the concepts of the present disclosure are susceptible to various modifications and alternative forms, specific exemplary embodiments thereof have been shown by way of example in the drawings and will herein be described in detail. It should be understood, however, that there is no intent to limit the disclosure to the particular forms disclosed, but on the contrary, the intention is to cover all modifications, equivalents, and alternatives following within the spirit and scope of the invention as defined by the appended claims.

Figure 4:
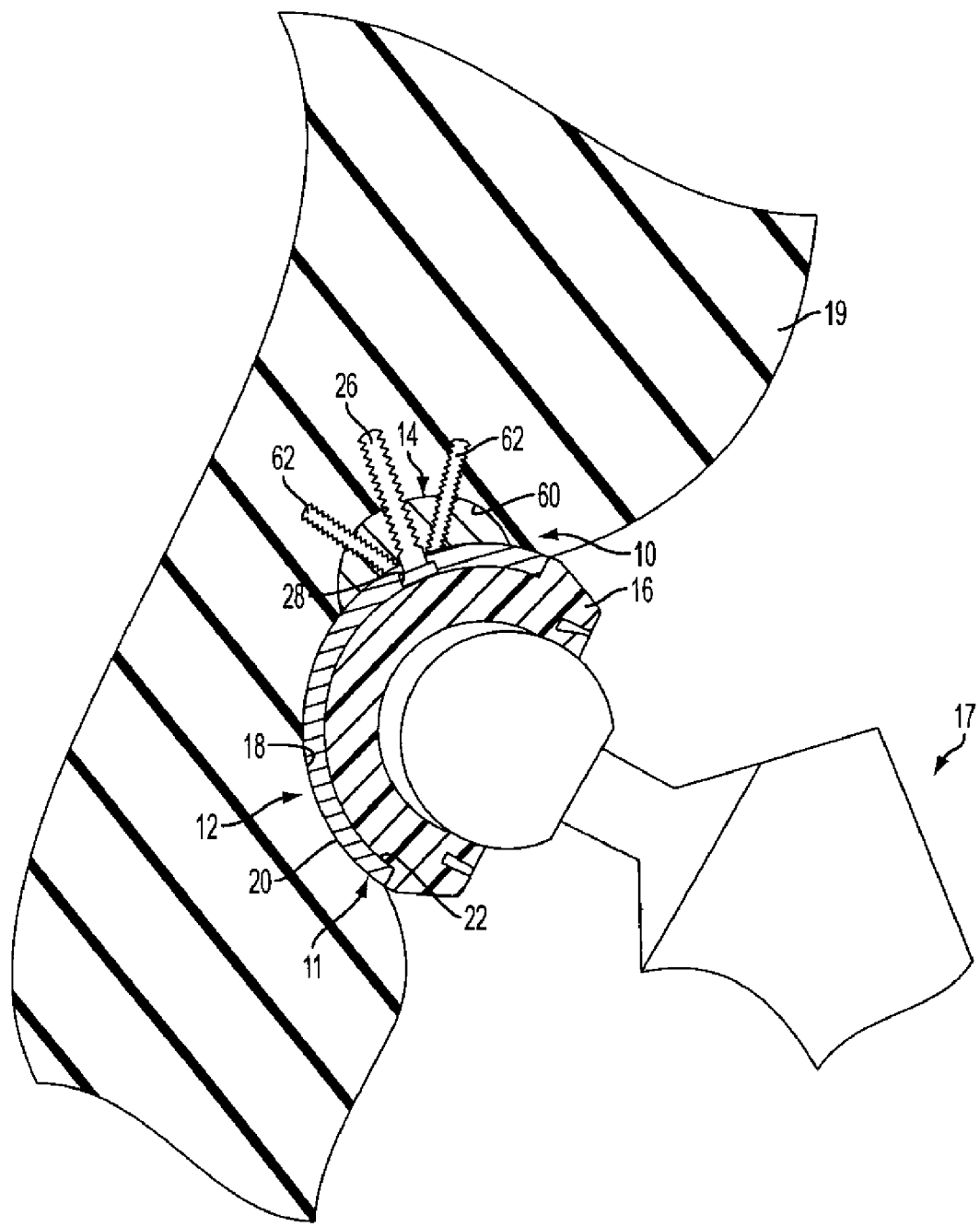
FIG. 4 is an assembled, sectional view of the acetabular prosthesis system implanted into a patient's acetabulum.

An acetabular prosthesis system 10 includes a modular cup 11 having an acetabular shell 12 and an augment component 14, as shown in FIGS. 1 and 4. The modular cup may also include a liner, such as the exemplary liner 16 shown in FIG. 4, coupled to the shell 12. The system 10 further includes a fastener 26 configured to couple the shell 12 and the augment component 14 together. The system 10 provides an acetabular prosthesis for implantation in an acetabulum, such as the acetabulum 18 shown in FIG. 4, and the surrounding hipbone 19. The system 10 described herein may be used in primary as well as revision hip implant procedures where minor or significant bone tissue loss has occurred in or around the acetabulum. Illustratively, as is discussed in greater detail below, the augment component 14 is provided to replace and fill such areas where bone tissue loss has occurred while the modular cup is provided to fit within the acetabulum and mate with a corresponding femoral prosthetic component such as the exemplary femoral component 17 shown in FIG. 4.

The shell 12 of the acetabular cup is generally hemispherical in shape and includes a curved, convex outer surface 20 and a curved, concave inner surface 22. As is discussed in greater detail below, the convex outer surface 20 is configured to be received within the acetabulum 18 of the patient during the hip replacement procedure. Illustratively, the shell 12 is made from a biocompatible metal such as such as titanium, titanium alloys, stainless steel, cobalt-chromium alloys, for example. However, the shell 12 may be made from any other suitable biocompatible material as well including ceramics and plastics, for example. Further, the shell 12 may be made from a porous metal scaffold or foam. This porous metal may comprise stainless steel, titanium, titanium alloys, cobalt-chromium alloys, and other materials that are suited for use in a biocompatible environment. For example, the porous metal scaffold may be a "titanium foam" material described, for example, in U.S. patent application Ser. No. 11/677,140 titled "Porous Metal Foam Structures and Methods" and assigned to the same assignee as the present application, the disclosure of which is incorporated by reference herein. Accordingly, therefore, it is within the scope of this disclosure to include a shell 12 made from any biocompatible porous or non-porous material. The shell 12 may also include a biocompatible porous or non-porous coating thereon.

As noted above, the shell 12 of the acetabular cup is typically associated with a bearing liner, such as the liner 16 shown in FIG. 4. While such bearing liners are typically made from a biocompatible polymer, a bearing liner for use with the shell 12 may be made from any suitable biocompatible material. The bearing liner may be coupled to the inner surface 22 of the shell 12 through the use of a retaining ring lock or bone cement, for example.

The illustrative shell 12 includes a plurality of apertures 24 extending through the outer surface 20 and the inner surface 22 of the shell 12. While the shell 12 disclosed herein includes thirteen apertures 24, it is within the scope of this disclosure to provide a shell including any number of apertures. For example, it is contemplated that a shell including one or more apertures may be provided. It is further within the scope of this disclosure to locate the apertures of the shell in any suitable orientation. Furthermore, as is discussed below, it is within the scope of this disclosure to provide a shell without any apertures formed through the inner and outer surfaces of the curved body of the shell.

Illustratively, the apertures 24 are each able to receive the fastener 26 therethrough in order to couple the shell 12 to the acetabulum 18. Furthermore, the apertures 24 may also allow for bone cement infiltration in procedures where bone cement (not shown) is used to attach the shell 12 to the acetabulum 18 and/or to attach the bearing liner 16 to the shell 12. Finally, the apertures 24 may also allow for bone tissue in-growth.

As shown in FIG. 1, the apertures 24 of the shell 12 are defined by a smooth sidewall 27. However, it is within the scope of this disclosure to include a shell 12 having one or more bores which define a threaded surface. Each aperture 24 further includes a recessed area 28 defined by the smooth sidewall 27 and formed in the inner surface 22 of the shell 12. The recessed area 28 is provided to receive the head 31 of the screw 26 therein in order to maintain a generally smooth inner surface 22 of the shell 12 when the shell 12 is coupled to both the augment component 14 and to the patient's hipbone 19.

The augment component 14 is provided to fill any defects within the patient's hipbone 19. As is described in greater detail below, the surgeon may fill a defective area of the acetabulum 18 or surrounding hipbone 19 with one or more augment components. Illustratively, the augment component 14 is generally wedge-shaped. However, the augment component 14 may be any suitable shape or size to fill a defective area of the acetabulum 18 having any shape or size.

Illustratively, the augment component 14 is made from a porous metal scaffold material such as the "titanium foam" material described above. However, it is within the scope of this disclosure to provide an augment component 14 made from any biocompatible porous metal as well as any other biocompatible porous material that provides suitable bone ingrowth. Alternatively, the augment component 14 may be made from a biocompatible solid material and or a solid material having a porous coating thereon. Accordingly, as with the shell 12, it is within the scope of this disclosure for the augment component 14 to be made from any suitable biocompatible porous or non-porous material.

Figure 2:
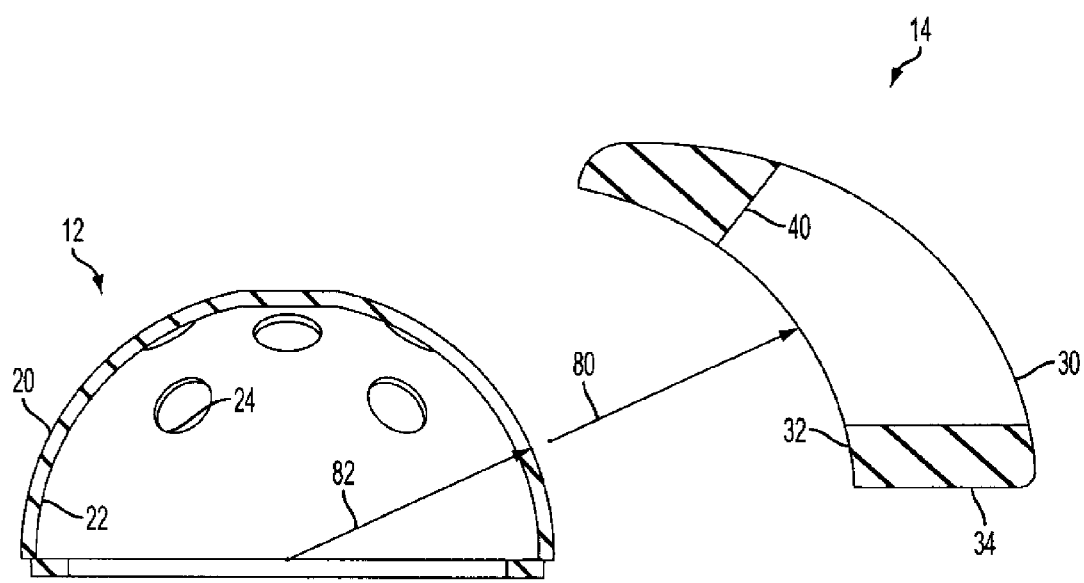
FIG. 2 is a sectional view of the acetabular shell and augment component.

As shown in FIGS. 1-3C, the augment component 14 includes a curved outer surface 30, a curved inner surface 32, and an end surface 34. Illustratively, the augment component 14 defines a wedge-shaped portion of a generally hemispherical component. However, as noted above, the augment component 14 may define any suitable shape or size. For example, the augment component 14 may be generally rectangularly shaped, oval shaped, square shaped, or the like. Illustratively, as shown in FIG. 2, the inner surface 32 of the augment component 14 has a radius of curvature 80 generally the same as or substantially similar to a radius of curvature 82 of the outer surface 20 of the shell 12. As such, in use, the outer surface 20 of the shell 12 is engaged with and substantially conforms to the inner surface 32 of the augment component 14, as shown in FIGS. 4 and 5-7, for example. However, it is within the scope of this disclosure to include a system wherein the radius of curvature of the inner surface of the augment component is smaller than the radius of curvature of the outer, curved surface of the shell. For example, the radius of curvature of the inner surface of the augment component may be approximately 90%-100% of the radius of curvature of the outer, curved surface of the shell. In such a system, the augment component becomes slightly deformed when the system is assembled and the augment component is coupled to the shell in order to fit onto the outer, curved surface of the shell. This slight deformation of the augment component causes the augment component to "pinch" the shell when the two components are secured together. Accordingly, this pinching action of the augment component on the shell operates to further secure the augment component and the shell to each other.

Figure 3A:
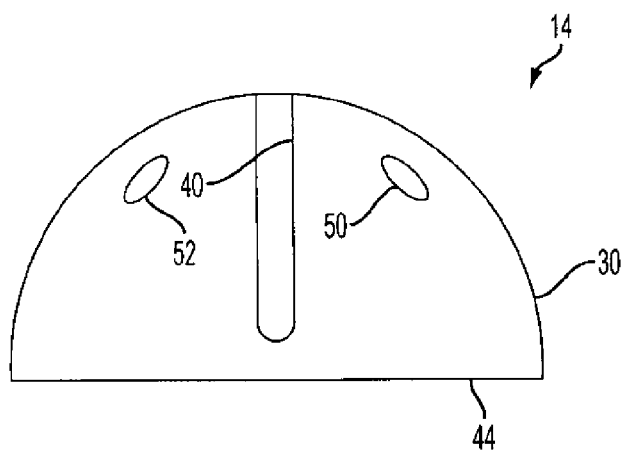
FIG. 3A is a front view of the augment component.
Figure 3B:
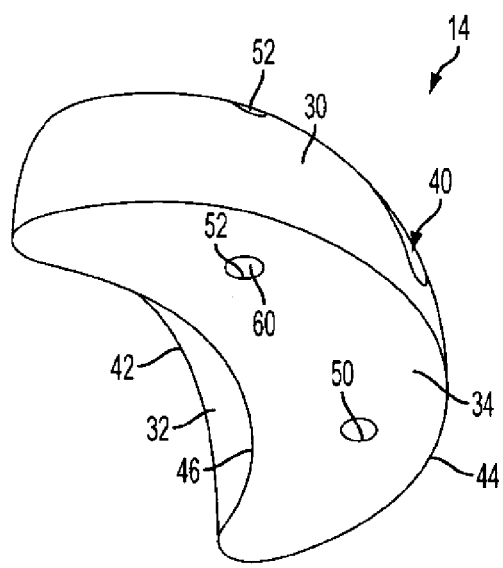
FIGS. 3B and 3C are perspective views of the augment component.
Figure 3C:
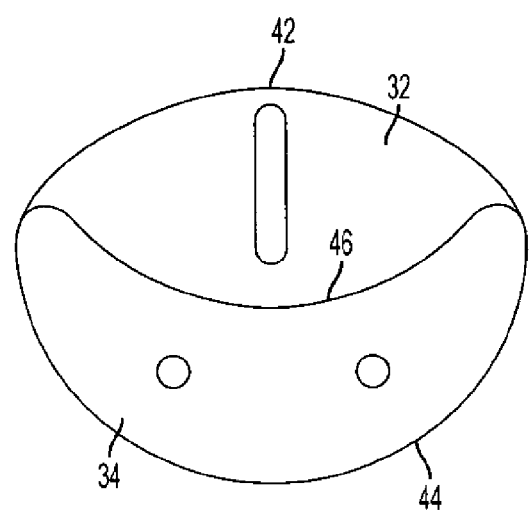

The augment component 14 further includes a slot 40 formed through and extending between the curved outer surface 30 and the curved inner surface 32. Illustratively, the slot 40 is linear and is oriented to define a plane generally perpendicular to the end surface 34 of the augment component 14. Further illustratively, as shown in FIGS. 3A and 3C, the slot 40 extends through the outer and inner curved surfaces 30, 32 in an up and down direction between a top edge 42 and a bottom outer edge 44 of the end surface 34 of the augment component. Further, as shown in the bottom perspective view of the augment component 14 in FIG. 3C, the slot 40 extends through the outer and inner curved surfaces 30, 32 in an up and down direction between an inner edge 46 of the end surface 34 of the augment component 14 and the top edge 42 of the augment component 14. However, it is within the scope of this disclosure for the augment component 14 to include a slot in any location and any orientation. For example, it is within the scope of this disclosure to provide an augment component including a slot defining a plane generally parallel to or angled at any degree to the end surface of the augment component. It is also within the scope of this disclosure to include a slot extending through the augment component from any outer surface of the augment component to any other outer surface of the augment component 14.

Illustratively, the slot 40 is sized to receive the fastener 26 in order to couple the shell 12 and the augment component 14 to each other. As shown and described above in reference to FIG. 1, the illustrative fastener 26 is a self-tapping bone screw configured to self-tap into the titanium foam material of the augment component 14 as the fastener 26 is drilled into the slot. However, it is within the scope of this disclosure for the fastener to be any type of bone screw, locking screw, nut and bolt, etc. suitable for securing the augment component 14 and the shell 12 together. It should be understood that the particular size (e.g., the width) of the slot may be configured to receive any suitable fastener therein. Further, the size of the slot may be varied to maximize both the ease of insertion of the fastener as well as the retention of the fastener with the slot. For example, it may be more difficult to drill a screw through a narrow slot relative to the size of the fastener; however, such a narrow slot may operate to better bite and retain the fastener therein. Conversely, a wider slot may be easier for a surgeon or other technician to drill a fastener therethrough; however, such a wide slot may provide less stability between the fastener and the augment component. Accordingly, the size and shape of the slot may be varied to maximize both ease of insertion as well as strength and retention. The size and shape of the slot 40 may also be varied to accommodate fasteners of different sizes.

The augment component 14 further includes first and second bores 50, 52 extending from the outer, curved surface 30 to the generally flat end surface 34. As shown in FIG. 3A, the slot 40 is positioned between the first and second bores 50, 52. Furthermore, the longitudinal axes of the bores 50, 52 are parallel to each other and define a plane extending through the longitudinal axes of the bores 50, 52 that is perpendicular to the plane extending through the slot 40. Illustratively, while the bores 50, 52 extend from the outer, curved surface 30 to the end surface 34, it is within the scope of this disclosure to include an augment component 14 having bores which extend between any two surfaces thereof. Furthermore, while two bores 50, 52 are provided, it is within the scope of this disclosure to include an augment component 14 having any number of bores formed therein. Further illustratively, the bores 50, 52 are defined by a generally smooth inner surface 60; however, the bores 50, 52 may be defined by a threaded surface (not shown) as well. As is discussed in greater detail below, the bores 50, 52 are configured to receive a fastener, such as a bone nail or screw, in order to secure the augment component 14 to the patient's hipbone 19.

Figure 5:
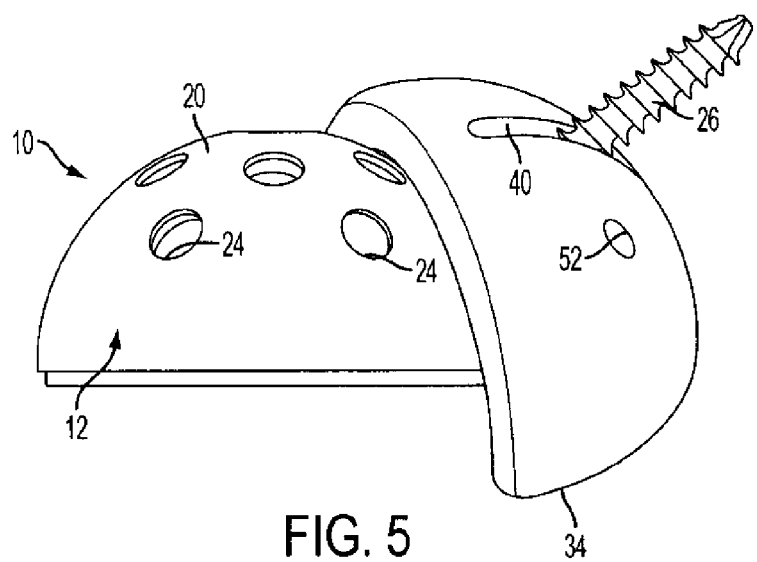
FIG. 5 is a perspective view of the system showing the shell and the augment component in a first orientation relative to each other.
Figure 6:
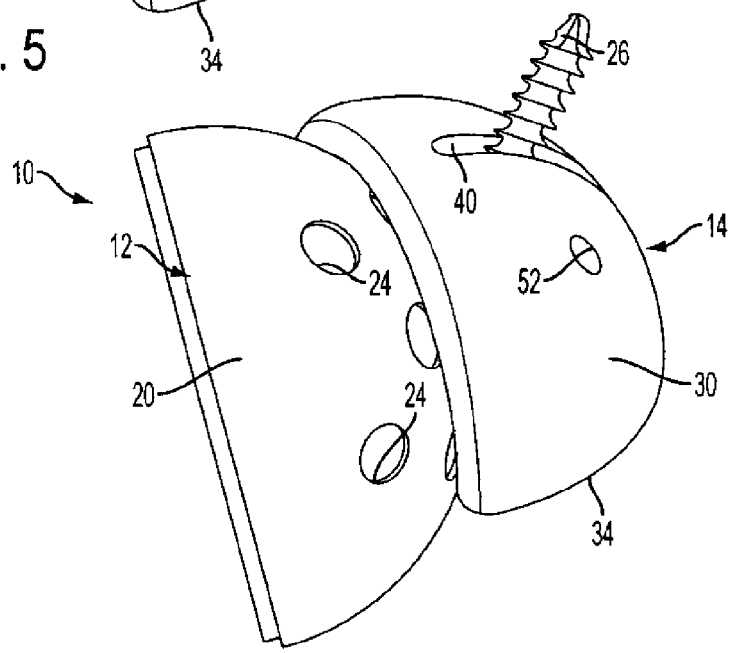
FIG. 6 is a perspective view similar to FIG. 5 showing the shell and the augment component in a second orientation relative to each other.
Figure 7:
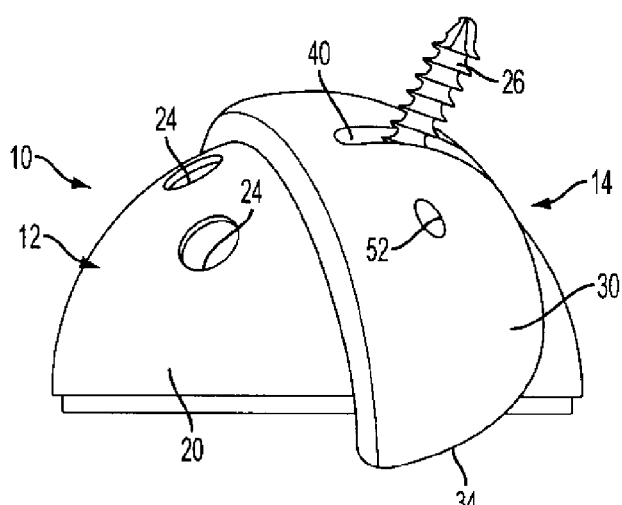
FIG. 7 is a perspective view similar to FIGS. 5 and 6 showing the shell and the augment component in a third orientation relative to each other.

In use, the shell 12 and augment component 14 may be oriented in any number of positions relative to one another. The shell 12 and the augment component 14 are each able to slide relative to one another in medial, lateral, anterior, posterior, superior, and inferior directions, and any combination thereof. Furthermore, the shell 12 and the augment component 14 are each able to rotate in clockwise or counterclockwise directions relative to each other in order to achieve a desired orientation of the two components for the patient. For example, as illustratively shown in FIGS. 5-7, the shell 12 is oriented in three different positions relative to the augment component 14. For example, FIG. 5 shows the shell 12 and the augment component 14 in a first illustrative orientation. The shell 12 is moved to a second illustrative position relative to the augment component 14 in FIG. 6. Illustratively, the shell 12 has rotated or slid to the right in a lateral direction from the position shown in FIG. 5 to the position shown in FIG. 6. Further, the shell 12 is shown in a third illustrative position relative to the augment component 14 in FIG. 7. Illustratively, the shell has rotated or slid in a forward or anterior direction while also sliding laterally from the position shown in FIG. 5.

As shown, the shell 12 may be rotated relative to the augment component 14 in any direction to allow the surgeon to properly place the shell 12 and augment component 14 relative to each other to provide a customized fit for the patient. Further, the shell 12 and augment component 14 may be oriented in any suitable position relative to one another such that any one of the apertures 24 of the shell 12 is aligned with the slot 40 of the augment component 14 in order to allow a surgeon or other technician to place a fastener through the particular bore of the shell 12 and into the slot 40 of the augment component 14 in order to couple the shell 12 and augment component 14 to each other. Further, the augment component 14 may be positioned in any location on both the generally peripheral position of the outer surface 20 of the shell 12 as well as the generally central portion of the outer surface 20 of the shell 12. In other words, the augment component 14 may be positioned in posterior, superior, inferior, anterior, medial, and lateral regions of the outer surface 20 of the shell 12. Accordingly, the slot 40 of the augment component 14 allows the surgeon to position the shell 12 in a wide variety of locations and orientations while still maintaining the ability to secure the shell 12 to the augment component 14 using a fastener, such as the screw 26.

During a hip replacement surgery, the surgeon or other technician may install the modular cup and augment system 10 in a number of different ways. In a first method, the surgeon removes the diseased or otherwise damaged bone from the patient's hipbone 19 in order to create a void, such as void 60 shown in FIG. 4, sized and shaped to receive the augment component 14 therein. The augment component 14 is then placed within the void 60 and secured to the hipbone 19 with the use of two fasteners, such as screws 62. While two screws 62 are shown, it is within the scope of this disclosure to use any suitable number of screws or other fasteners to secure the augment component 14 within the void 60. Illustratively, each screw 62 is self-threaded into one of the bores 50, 52 of the augment component 14 and then drilled into the patient's bone 19 to hold the augment component 14 securely in place. As noted above, the augment component 14 is made from a titanium foam material that allows the screws 62 to self-thread into the augment component 14 as they are placed through the bores 50, 52 and into the patient's hipbone 19. Bone cement (not shown) may be used in addition to or in place of the screws 62 to secure the augment component 14 to the patient's bone 19.

Next, the shell 12 is oriented relative to the augment component 14 to a position selected by the surgeon or their technician. As noted above, the shell 12 may be placed in any number of different positions relative to the augment component 14 and may be rotated in any number of directions in order to achieve the proper placement of the shell 12 within the acetabulum to best accommodate the patient's natural anatomy. Once the shell 12 is properly placed, a fastener, such as a bone nail (not shown) or the screw 26, is placed through one of the apertures 24 of the shell 12, which is aligned with the slot 40 of the augment component 14. Illustratively, as shown in FIG. 4, the screw 26 is also drilled into the hipbone 19 of the patient to further secure the shell 12 and augment component 14 to each other and to the patient. However, it is within the scope of this disclosure to use a shorter screw that couples only the shell 12 to the augment component 14 and does not extend into the patient's hipbone 19. After the shell 12 is secured to the augment component 14, the shell 12 may be further secured to the surrounding hipbone 19 by placing one or more additional fasteners through other apertures 24 of the shell 12 directly into the patient's hipbone 19.

Once the final position of the shell 12 is determined, the surgeon or other technician can then secure the shell 12 to the augment component 14 by inserting a fastener 26, such as a surgical screw, through one or more of the apertures 24 of the shell 12 which generally align with the slot 40 of the augment component 14. The screw 26 may extend upwardly through the shell 12 and the augment component 14 with the screw tip not extending past the outer, curved surface of the augment component 14. Alternatively, the screw may be sized such that the screw tip extends through the shell 12 and the augment component 14 beyond the outer, curved surface 30 of the augment component 14 to secure into the patient's surrounding bone 19 as well.

Alternatively, the surgeon or other technician may first secure the shell 12 into the acetabulum 18 of the patient's hipbone 19 using one or more fasteners, such as the bone screw 26. Here, the surgeon first orients the shell 12 in the position which best accommodates the patient's natural anatomy then secures the shell 12 to the patient's hipbone 19. Once the shell 12 is properly secured in the desired location and orientation, the surgeon may then remove any damaged or diseased bone around the shell 12 to create a void, such as the void 60, sized and shaped to receive one or more augment components 14 therein. The augment component 14 is then placed within the newly-created void 60 and is secured to the already-placed shell 12 through the use of a fastener such as screw 26. As discussed above, the fastener 26 is received through one of the apertures 24 of the shell 12, which is aligned with the slot 40 of the augment component 14 in order to secure the shell 12 and the augment component 14 together. This screw 26 may also be driven into the patient's bone to further secure the shell 12 and augment component 14 to the patient's hipbone 19.

An additional method of performing the hip replacement procedure includes securing the shell 12 to the augment component 14 using a fastener at a "back table" away from the actual surgery site. At the back table, the surgeon is able to properly orient the shell 12 and augment component 14 relative to one another before securing the augment component 14 and shell 12 together. Prior to coupling the shell 12 and component 14 together at the back table, the surgeon may fit the augment component 14 into the void 60 already created in the patient's hipbone 19 and may place the shell 12 in the desired position to mark the placement of the augment component 14 and shell 12 relative to each other. Marking the shell 12 and/or the augment component 14 allows the surgeon to properly re-orient the two components relative to each other when securing the shell 12 and the augment component 14 together at the back table away from the surgery site. Once the augment component 14 and shell 12 have been coupled together, the surgeon then places the assembled system 10 into the patient's hipbone 19. The surgeon may then place additional fasteners through the shell 12 and the augment component 14 to secure the augment component 14 and the shell 12 to the patient's surrounding hipbone 19. Additional fasteners may be used to further secure the shell 12 directly to the surrounding bone 19.

As is noted above, the surgeon may also use bone cement (not shown) to secure the augment component 14 to the patient's bone 19 and to secure the shell 12 to the augment component 14. Further, although only one augment component 14 is shown to be coupled to the shell 12, it is within the scope of this disclosure to use any number of augment components 14 with the shell 12 in order to fill multiple defects and/or larger defects in a patient's bone 19.

Figure 8:
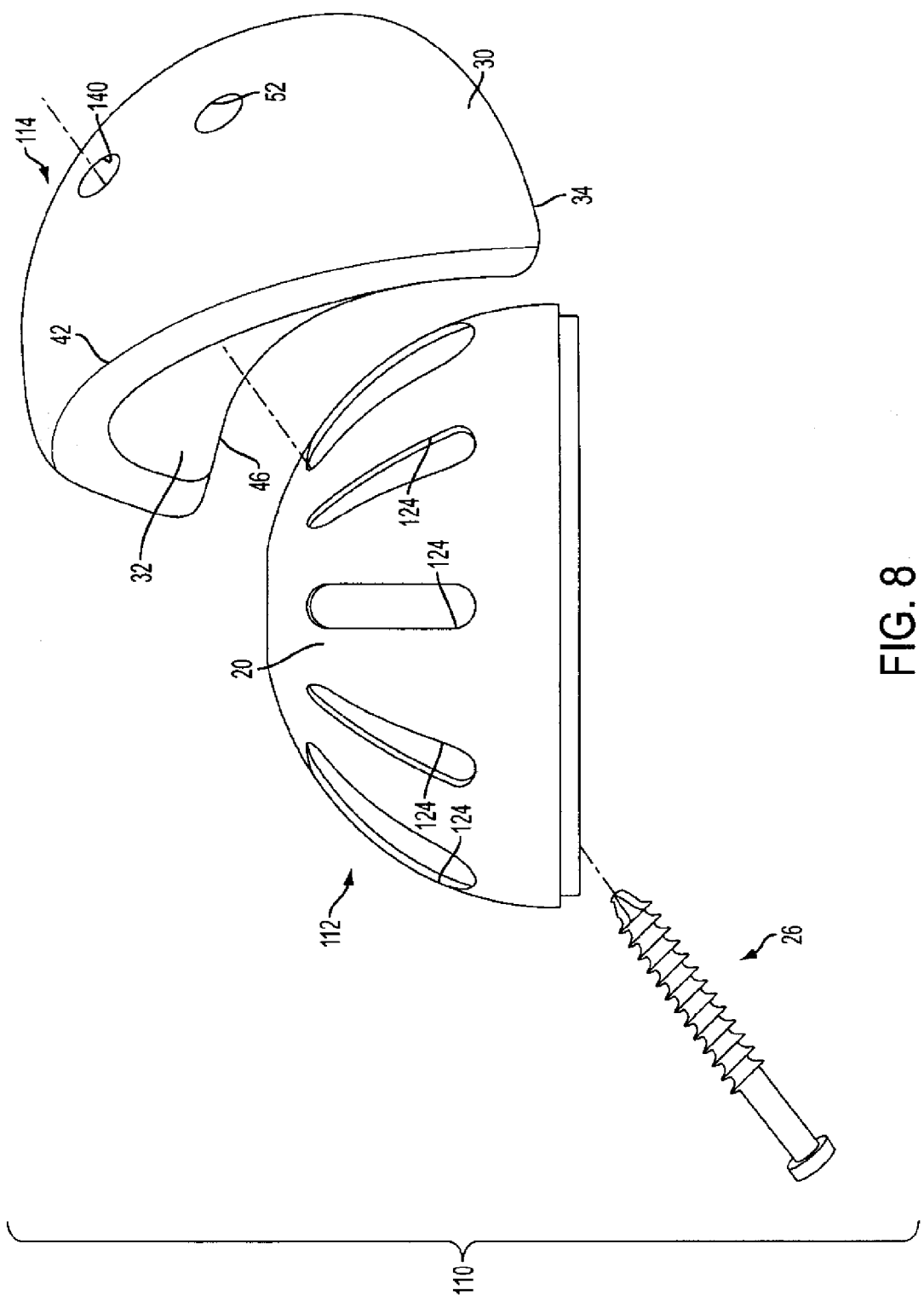
FIG. 8 is an exploded, perspective view of another acetabular prosthesis system of the present disclosure.

Looking now to FIG. 8, an alternative modular cup and augment system 110 includes a shell 112 and an augment component 114. Illustratively, the shell 112 and augment component 114 each include certain features that are the same as or similar to features of the shell 12 and augment component 14 discussed above. As such, like reference numerals are used to denote like components. As shown in FIG. 8, the shell 112 includes a plurality of slots 124 formed through the outer surface 20 and the inner surface 22. Such slots 124 are provided to receive one or more fasteners, such as the bone screw 26, therethrough, in order to couple the shell 112 to the augment component 114 as well as to the patient's hipbone 19.

Illustratively, the augment component 114 of the system 110 includes the bores 50, 52 as well as a single, central bore 140 positioned between the bores 50, 52. Similar to that discussed above in regards to the augment component 14, the bores 50, 52 are configured to receive a fastener therethrough to secure the augment component 114 to the patient's hipbone 19. The central bore 140, however, is provided to receive the fastener 26 therein in order to couple the shell 112 and the augment component 114 to each other. Accordingly, while the system 10 shown in FIGS. 1-7 includes the shell 12 having a plurality of apertures 24 and the augment component 14 including the slot 40, the system 110 shown in FIG. 8 includes the shell 112 including a plurality of slots 124 (rather than the apertures 24 of the shell 12) and the augment component 114 including a single bore 140 (rather than the slot 40 of the augment component 14). As such, the augment component 114 is similarly able to be placed in any suitable location on the outer surface 20 of the shell 112 provided that at least a portion of one of the slots 124 of the shell 112 is aligned with the bore 140 of the augment component.

Illustratively, the plurality of slots 124 of the shell 112 are shown in FIG. 8 to be arranged in a particular pattern. It is within the scope of this disclosure, however, to include a shell having one or more slots formed through the outer and inner surfaces 20, 22 thereof which are arranged in any suitable pattern. In other words, the slot or slots 124 of the shell 112 may be arranged to extend in various different directions relative to one another and may or may not be interconnected. Furthermore, while the bore 140 of the augment component 114 is generally centrally-located between the two bores 50, 52, it is within the scope of this disclosure to provide an augment component having one or more bores each configured to receive a fastener for coupling the augment component to the shell in any suitable location.

Figure 9:
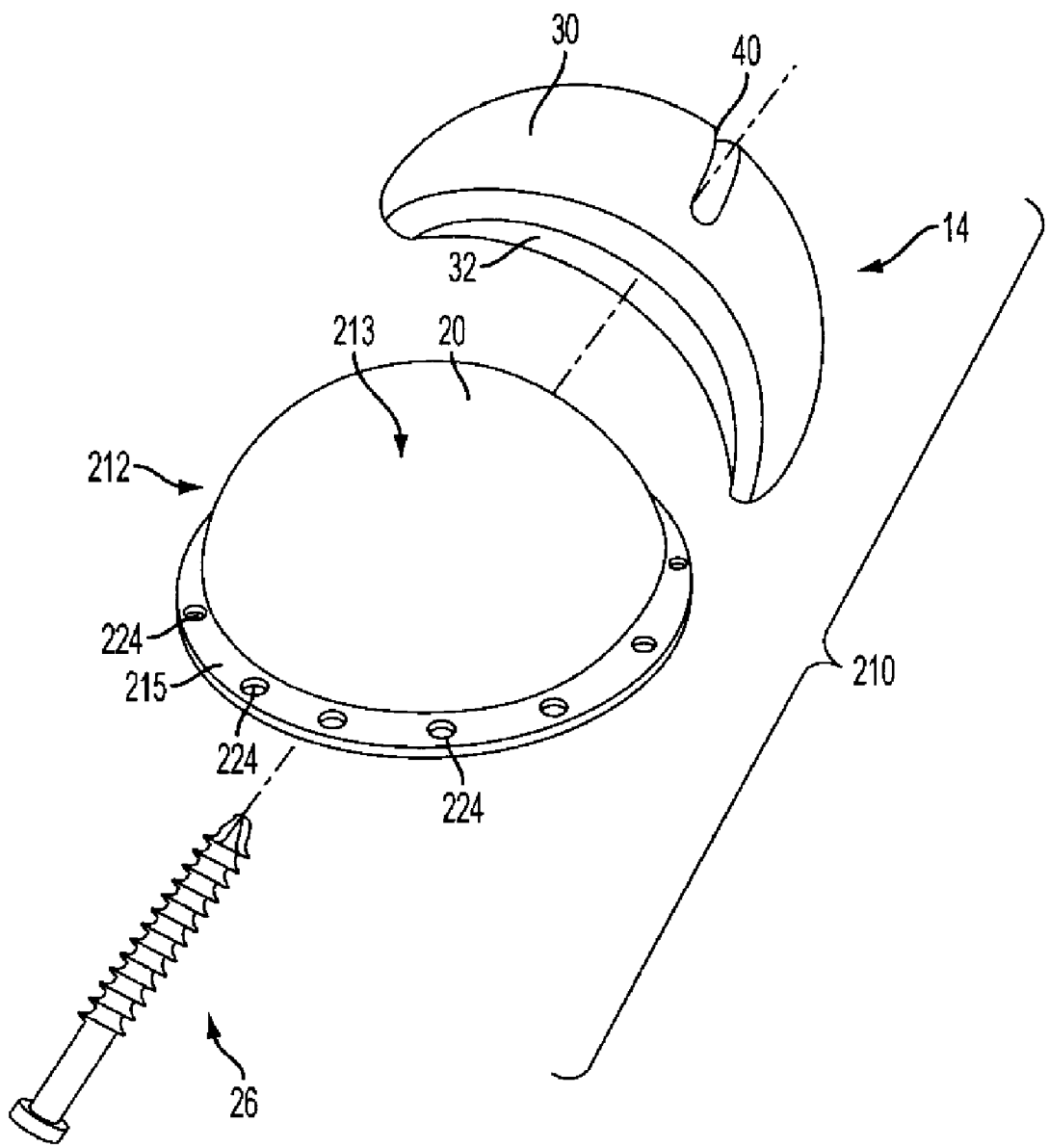
FIG. 9 is an exploded, perspective view of yet another acetabular prosthesis system of the present disclosure.

Looking now to FIG. 9, another modular cup and augment system 210 includes an alternative shell 212 and the augment component 14. Illustratively, the shell 212 includes a curved body 213 defining the outer curved surface 20 and the inner curved surface 22. Unlike the shells 12, 112, discussed above, the shell 212 does not include any aperture, such as apertures 24, or slot, such as slots 124, therethrough. Further illustratively, the shell 212 includes a body 213 and a rim 215 coupled to an outer, peripheral end of the body 213, as shown in FIG. 9. Illustratively, the body 213 of the shell 212 is made from the porous titanium foam disclosed above; however, it is within the scope of this disclosure for the shell 212 to be made from any suitable biocompatible porous material. The rim 215, on the other hand, is made from a biocompatible metal such as stainless steel, titanium, cobalt-chrome, or other such alloys, for example. However, the rim 215 may be made from a porous material as well. The rim includes a plurality of bores 224 formed therethrough. The bores 224 are configured to receive a fastener in order to secure the shell 212 to the patient's bone 19.

In use, the surgeon implants the augment component 14 in the void 60 created in the surgically-prepared acetabulum 18' of the patient's hipbone 19 of the patient, as discussed above, and then aligns the shell 212 relative to the augment 14 to determine the proper positioning of the shell 212 to best suit the patient's anatomy. Once the shell 212 is properly positioned, the surgeon may place a marking on the shell 212 to denote the location of one or more holes to be drilled by the surgeon through the shell body 213 which would align with the slot 40 of the augment component 14. The surgeon then drills the hole or holes through the shell body 213 at the site of the indicated markings on the shell body 213. The drilling of the hole or holes may be conducted at the "back table" rather than within the patient himself. Once the hole or holes have been drilled, the surgeon places the shell 212 within the patient and secures a fastener, such as the fastener 26, through each of the recently drilled holes in the shell body 213 and the slot 40 in the augment component 40.

Alternatively, the surgeon may position, but not secure, the augment component 14 and the shell 212 within the patient and mark the shell 212 and/or the augment component 14 in order to indicate the relative positioning of the shell 212 and the augment component 14 to each other. As noted above, the surgeon may also indicate on the shell body 213 where one or more holes may be drilled in alignment with the slot 40 of the augment component 14 in order to couple a fastener to the shell 212 and component 14. The surgeon may then drill a pilot hole or holes through the shell body 213 at the back table and may further assemble the system 210 together at the back table prior to implanting the system 210 into the patient. As such, the shell 212 and augment component 14 are assembled outside the patient by placing a fastener through each of the pilot holes drilled through the shell body 213 and into the slot 40 of the augment component 14. Finally, the assembled shell 212 and augment component 14 may be implanted into the patient. The shell 212 is secured to the patient by securing fasteners through the bores 224 in the rim 215 of the shell 212.

As discussed above, the acetabular prosthesis systems 10, 110, 210 disclosed herein each allow a surgeon to position the respective shell 12, 112, 212 and augment component 14, 114 in any number of orientations relative to one another. This allows the surgeon the option of positioning the respective augment component 14, 114 in nearly any location on the outer curved surface 20 of the shell 12, 112, 212 without limitation. As noted above, the shell 12, 112, 212 and the augment component 14, 114 may be positioned in any orientation that aligns the slot 40 or bore 140 of the augment component 14, 114 with at least one aperture 24 or slot 124 of the shell 12, 112, 212 in order to provide a means by which a fastener can be used to couple the shell 12, 112, 212 and the augment component 14, 114 together. Accordingly, the acetabular prosthesis system 10 of the present disclosure provides many orientations by which a surgeon may to secure the augment component 14, 114 and the shell 12, 112, 212 together using an external fastener in addition to or instead of using bone cement. As such, a surgeon or other technician is able to place the acetabular shell 12, 112, 212 in any orientation to mimic the patient's natural anatomy and can mechanically fix the shell to the augment.

While the concepts of the present disclosure have been illustrated and described in detail in the drawings and foregoing description, such an illustration and description is to be considered as exemplary and not restrictive in character, it being understood that only the illustrative embodiments have been shown and described and that all changes and modifications that come within the spirit of the disclosure are desired to be protected.

There are a plurality of advantages of the concepts of the present disclosure arising from the various features of the systems described herein. It will be noted that alternative embodiments of each of the systems of the present disclosure may not include all of the features described yet still benefit from at least some of the advantages of such features. Those of ordinary skill in the art may readily devise their own implementations of a system that incorporate one or more of the features of the present disclosure and fall within the spirit and scope of the invention as defined by the appended claims.

The invention claimed is:

1. An acetabular prosthesis system configured to be coupled to a surgically-prepared acetabulum of a patient's hipbone comprising:
    an acetabular shell including an outer curved surface configured to engage the surgically prepared acetabulum, an inner curved surface, and a plurality of apertures extending through the outer curved surface and the inner curved surface;
    an augment component configured to be received within a void created in the surgically-prepared acetabulum, the augment component including an inner curved surface engaged with the outer curved surface of the acetabular shell, an outer surface, and a slot extending through the inner curved surface of the augment component and the outer surface of the augment component; and
    a first threaded fastener extending through at least one of the plurality of apertures of the acetabular shell and the slot of the augment component such that a tip of the first threaded fastener extends beyond the outer surface of the augment component,
    wherein the first threaded fastener is self-tapped into the slot of the augment component to secure the acetabular shell and the augment component together.

2. The acetabular prosthesis system of claim 1, wherein the augment component includes a bore configured to receive a second fastener therethrough.

3. The acetabular prosthesis system of claim 2, wherein the bore of the augment component is non-threaded.

4. The acetabular prosthesis system of claim 1, wherein the outer surface of the augment component is curved and wherein the augment component further includes a generally flat end surface.

5. The acetabular prosthesis system of claim 4, wherein the slot defines a plane generally perpendicular to the generally flat end surface of the augment component.

6. The acetabular prosthesis system of claim 4, wherein a bore of the augment component extends through the outer curved surface of the augment component and the generally flat end surface of the augment component.

7. The acetabular prosthesis system of claim 1, wherein the augment component is made from a porous metal material.

8. The acetabular prosthesis system of claim 1, wherein the radius of curvature of the inner curved surface of the augment component is generally equivalent to the radius of curvature of the outer curved surface of the shell.

9. The acetabular prosthesis system of claim 1, wherein the radius of curvature of the inner curved surface of the augment component is approximately 90%-100% of the radius of curvature of the outer curved surface of the shell.

10. An acetabular prosthesis system configured to be coupled to a surgically-prepared acetabulum of a patient's hipbone comprising:
    an acetabular shell including an outer curved surface configured to engage the surgically-prepared acetabulum, an inner curved surface, and a slot extending through the outer curved surface and the inner curved surface;
    an augment component configured to be received within a void created in the surgically-prepared acetabulum of the patient's hipbone, the augment component including an inner curved surface engaged with the outer curved surface of the acetabular shell, an outer surface, and a bore extending through the inner curved surface of the augment component and the outer surface of the augment component; and
    a threaded fastener securing the acetabular shell to the augment component, wherein the threaded fastener extends through the slot of the acetabular shell and the bore of the augment component such that a tip of the threaded fastener extends beyond the outer surface of the augment component, and the threaded fastener is self-tapped into the bore of the augment component to secure the acetabular shell to the augment component.

11. The acetabular prosthesis system of claim 10, wherein a curved body of the acetabular shell is made from a porous metal material.

12. The acetabular prosthesis system of claim 11, wherein the porous material is titanium foam.

13. The acetabular prosthesis system of claim 10, wherein the acetabular shell is configured to be secured by the threaded fastener to the augment component in (i) a first orientation, (ii) a second orientation wherein the acetabular shell is moved in one of a medial and a lateral direction relative to the position of the acetabular shell in the first orientation, (iii) a third orientation wherein the acetabular shell is moved in one of an anterior and a posterior direction relative to the position of the acetabular shell in the first orientation, and (iv) a fourth orientation wherein the acetabular shell is moved in one of a superior and an inferior direction relative to the position of the acetabular shell in the first orientation.

* * * * *